United States Patent
Bridgeman et al.

(10) Patent No.: US 9,913,652 B2
(45) Date of Patent: Mar. 13, 2018

(54) DEVICE AND METHOD FOR OCCLUDING THE LEFT ATRIAL APPENDAGE

(71) Applicant: ATRITECH, INC., Plymouth, MN (US)

(72) Inventors: John B. Bridgeman, Minneapolis, MN (US); Gregg Sutton, Maple Grove, MN (US); Christopher J. Clark, St. Michael, MN (US)

(73) Assignee: Atritech, Inc., Plymouth, MN (US)

( * ) Notice: Subject to any disclaimer, the term of this patent is extended or adjusted under 35 U.S.C. 154(b) by 0 days.

(21) Appl. No.: 14/940,887

(22) Filed: Nov. 13, 2015

(65) Prior Publication Data

US 2016/0066922 A1    Mar. 10, 2016

Related U.S. Application Data

(63) Continuation of application No. 12/583,744, filed on Aug. 25, 2009, now abandoned.

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12172* (2013.01); *A61B 2017/00601* (2013.01); *A61B 2017/00632* (2013.01)

(58) Field of Classification Search
CPC .......... A61B 17/0057; A61B 17/12122; A61B 17/12172; A61B 2017/00601; A61B 2017/00632
See application file for complete search history.

(56) References Cited

U.S. PATENT DOCUMENTS

| | | |
|---|---|---|
| 5,375,612 A | 12/1994 | Cottenceau et al. |
| 6,689,150 B1 | 2/2004 | VanTassel et al. |
| 6,994,092 B2 | 2/2006 | van der Burg et al. |
| 2003/0023266 A1 | 1/2003 | Borillo et al. |
| 2003/0050685 A1* | 3/2003 | Nikolic ............ A61B 17/12022 623/1.11 |
| 2003/0181942 A1 | 9/2003 | Sutton et al. |
| 2004/0093012 A1 | 5/2004 | Cully et al. |
| 2004/0158274 A1 | 8/2004 | WasDyke |
| 2005/0015109 A1 | 1/2005 | Lichtenstein |
| 2005/0070952 A1 | 3/2005 | Devellian |
| 2005/0113861 A1 | 5/2005 | Corcoran et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0155323 A1 | 7/2006 | Porter et al. |
| 2009/0105747 A1 | 4/2009 | Chanduszko et al. |

\* cited by examiner

*Primary Examiner* — Alexander Orkin
(74) *Attorney, Agent, or Firm* — Seager, Tufte & Wickhem LLP

(57) ABSTRACT

An implantable medical device for insertion in the left atrial appendage includes a cap coupled to a frame. The cap constrains movement of the legs of the frame during collapse and expansion of the device, such that the device can be deployed, recalled and redeployed without the device being damaged or the legs of the frame getting tangled.

13 Claims, 16 Drawing Sheets

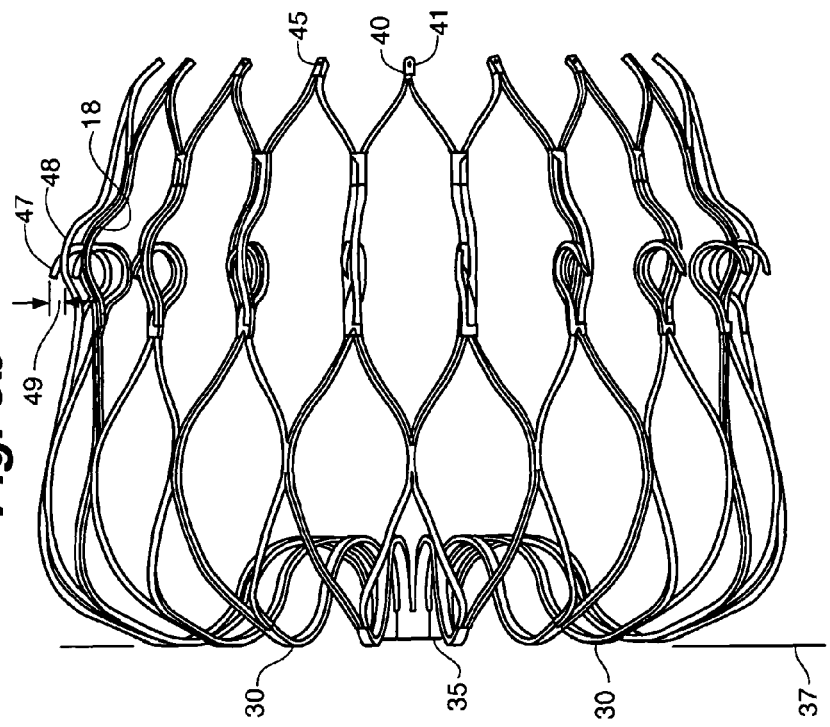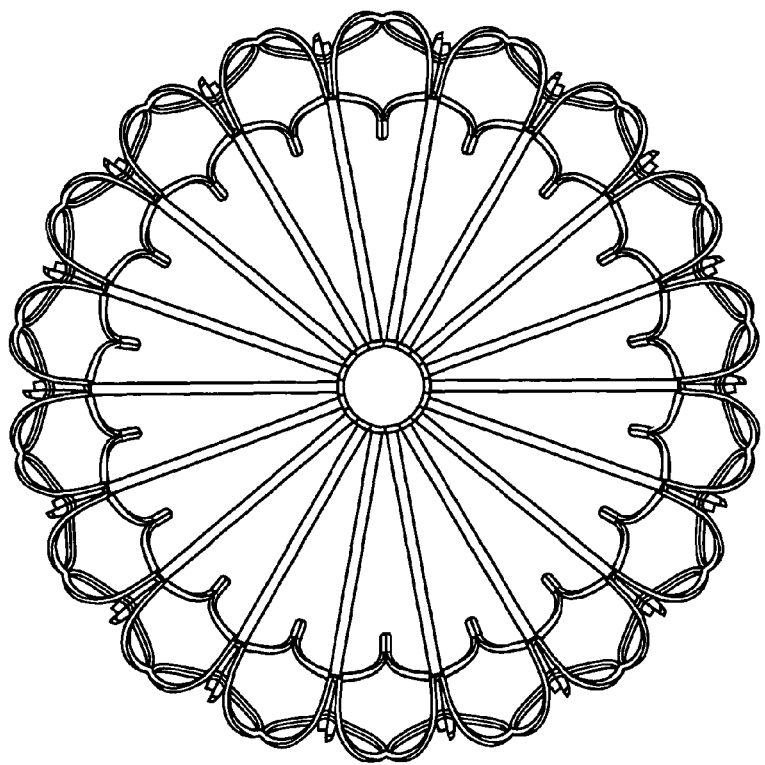

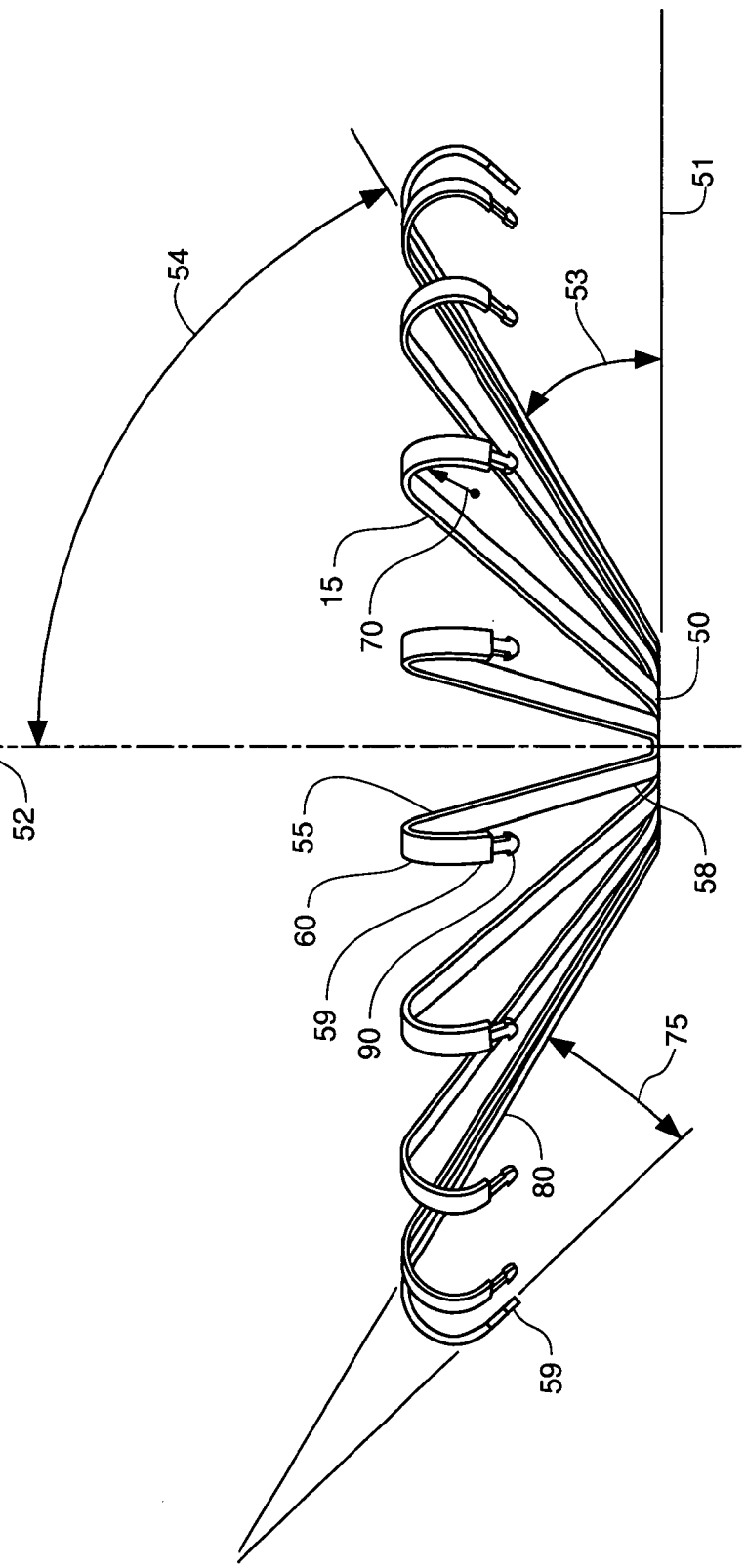

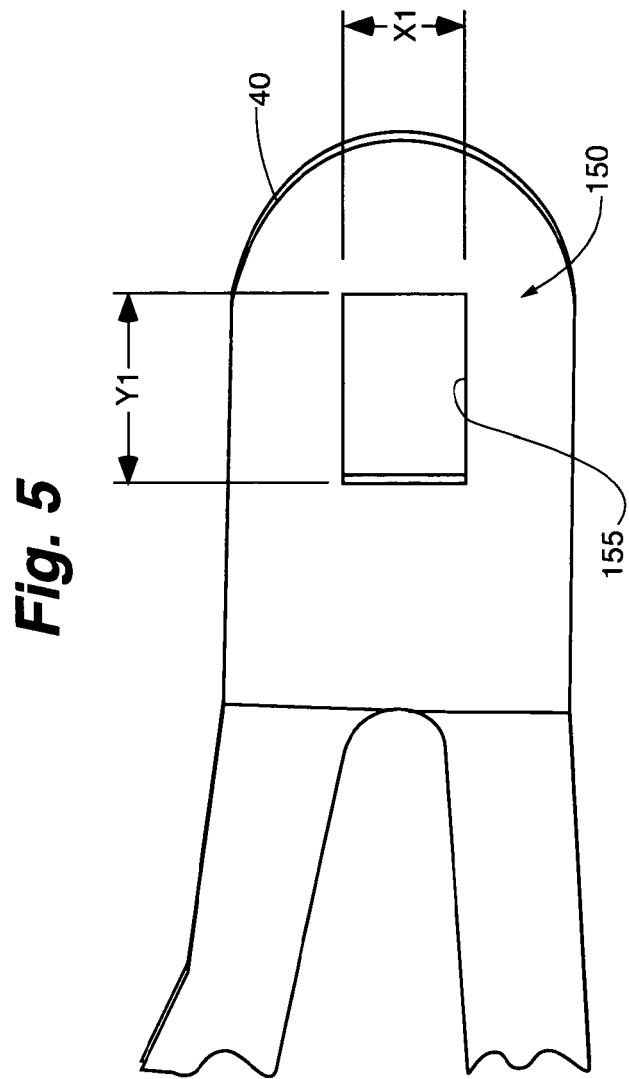

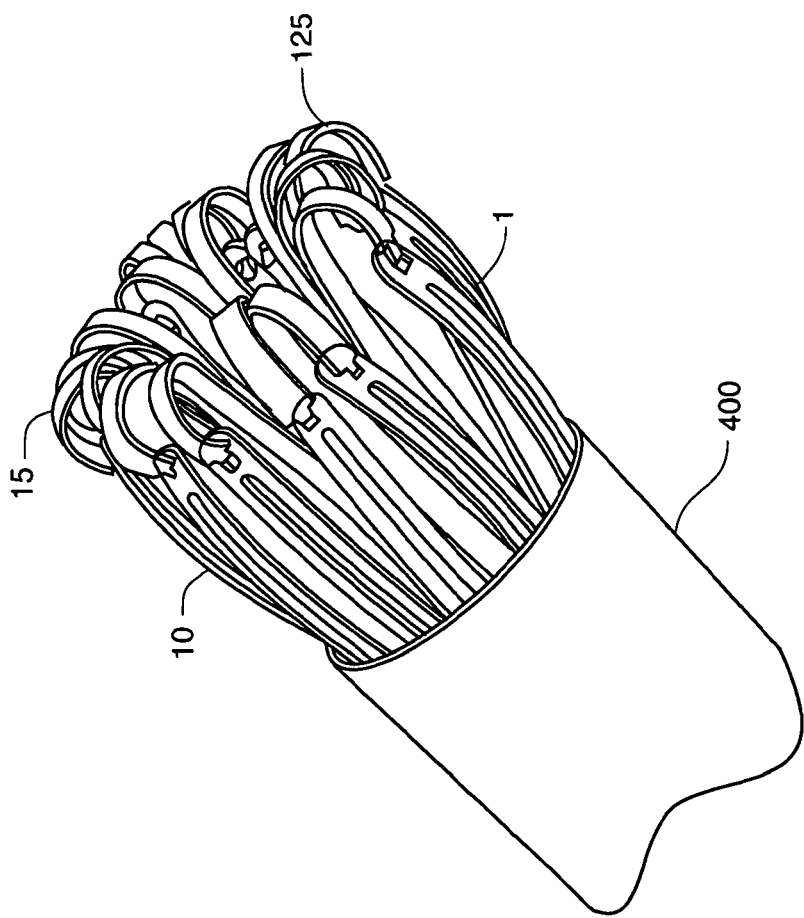
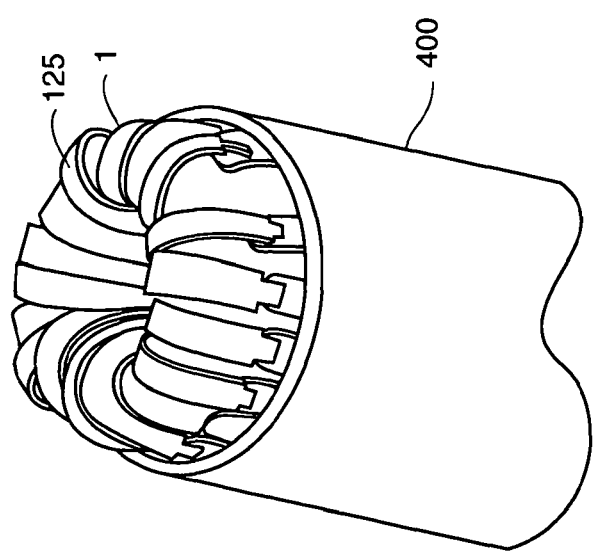

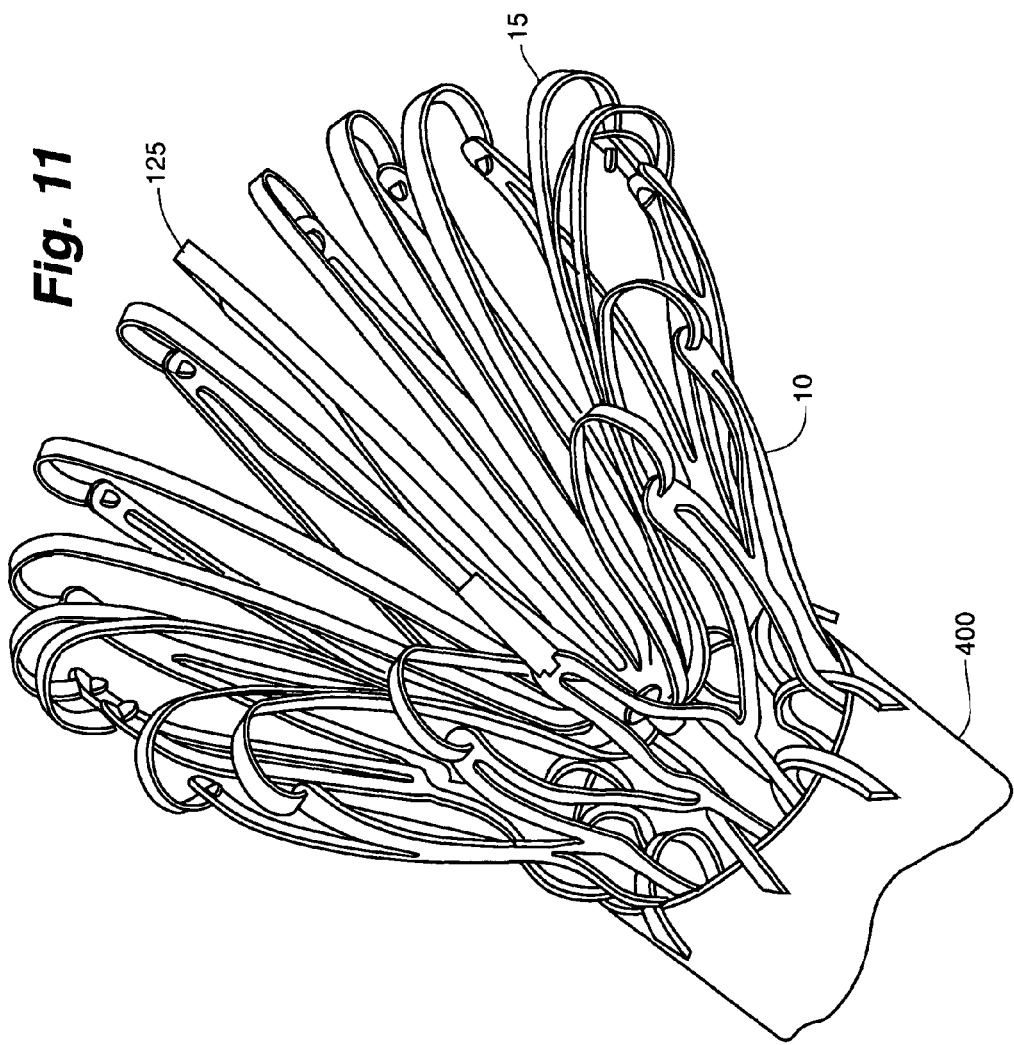

DEVICE AND METHOD FOR OCCLUDING THE LEFT ATRIAL APPENDAGE

RELATED APPLICATIONS

This application is a continuation of U.S. Ser. No. 12/583,744, filed Aug. 25, 2009.

FIELD OF THE INVENTION

An implantable medical device and method for occluding the left atrial appendage of a patient is disclosed.

BACKGROUND OF THE INVENTION

Implanted medical devices are available for insertion into the left atrial appendage (LAA). Such devices are used, for example, to block blood clots from passing out of the heart into the systemic circulation.

In general these devices are delivered to the LAA through a catheter system that enters the venous circulation and approaches the left atrium through the atrial septum between the right and left side of the heart. The catheter is guided through the septum toward the ostium of the left atrial appendage. After acquisition and insertion into the LAA the implanted medical device is deployed, and fixed so that it remains in the appendage. Once positioned, the implanted medical device is released by the catheter, and the catheter system is removed. Over time, the exposed surface structures of the implanted medical device spanning the ostium of the LAA becomes covered with tissue. This process is called endothelization.

SUMMARY OF THE INVENTION

There is a continuing need to improve these occlusion type implanted medical devices as well as the methods and catheter devices used to deliver them into the LAA. The preferred version of the device of the present invention is preferably formed as two separate metal pieces.

In practice a membrane-covered frame and a complimentary cap are linked or coupled together with a linkage. In one embodiment the linkage is a hinge mechanism. The assembled device has an expanded, deployed configuration and a collapsed, compressed configuration. It is biased into the expanded or deployed configuration by the superelastic nature of the frame material and processing. In the deployed configuration, the device, and more specifically, the membrane of the device, spans the ostium of the left atrial appendage. In the compressed configuration, the device fits within a delivery catheter for transport and delivery to the LAA. When the device is compressed within a delivery catheter, the cap folds inward and is carried within the interior of the frame.

The cap serves to regulate or control the deployment process and protects the attachment structures or retention members associated with the periphery of the device. The preferred retention structure is a series of barbs. These barbs penetrate tissue and retain the device in the interior of the left atrial appendage during implantation. The depth of the penetration is controlled or managed by a structural feature on the frame, while the retraction and recapture is managed by the cap which controls the barbs during recapture, when the device is withdrawn into the delivery catheter. This allows for redeployment and returns the barbs to their original functionality.

In general the occlusion membrane is attached to the frame by hooks or sutures. In one exemplary embodiment, the hooks are formed as a unitary piece of the frame, thereby simplifying the manufacture of the implanted medical device.

BRIEF DESCRIPTION OF THE DRAWINGS

Through he several figures of the drawing identical reference numerals indicate identical structures wherein:

FIG. 3A is an end view of the distal end of the frame;

FIG. 3B is a side view of the frame in isolation;

FIG. 4 is a side view of the cap in isolation;

FIG. 5 is a plan view of a hinge portion of the frame;

FIG. 9 is a perspective view of the IMD near the tip of the delivery catheter;

FIG. 10 is a perspective view of the IMD partially within a delivery catheter;

FIG. 11 is a perspective view of the IMD with the retention barbs emerging from the delivery catheter;

DETAILED DESCRIPTION OF A PREFERRED EMBODIMENT(S)

Figure 1B:
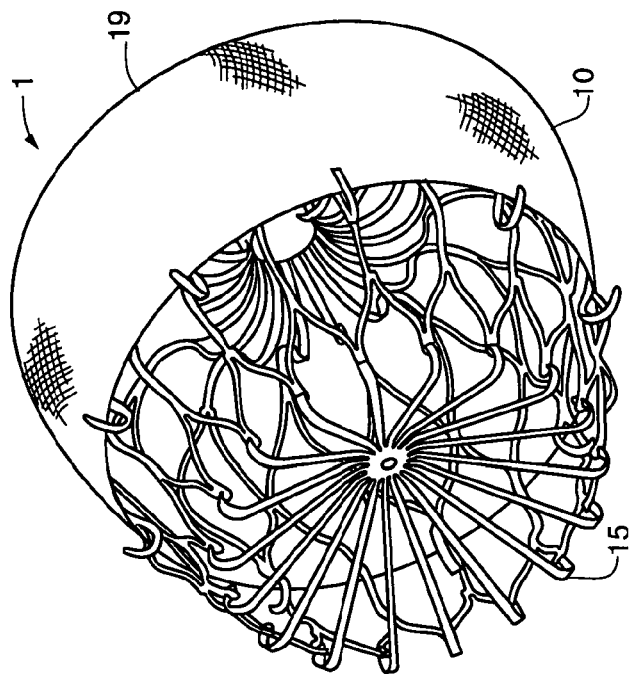
FIG. 1B is a perspective view of the IMD as seen from the distal end.
Figure 1A:
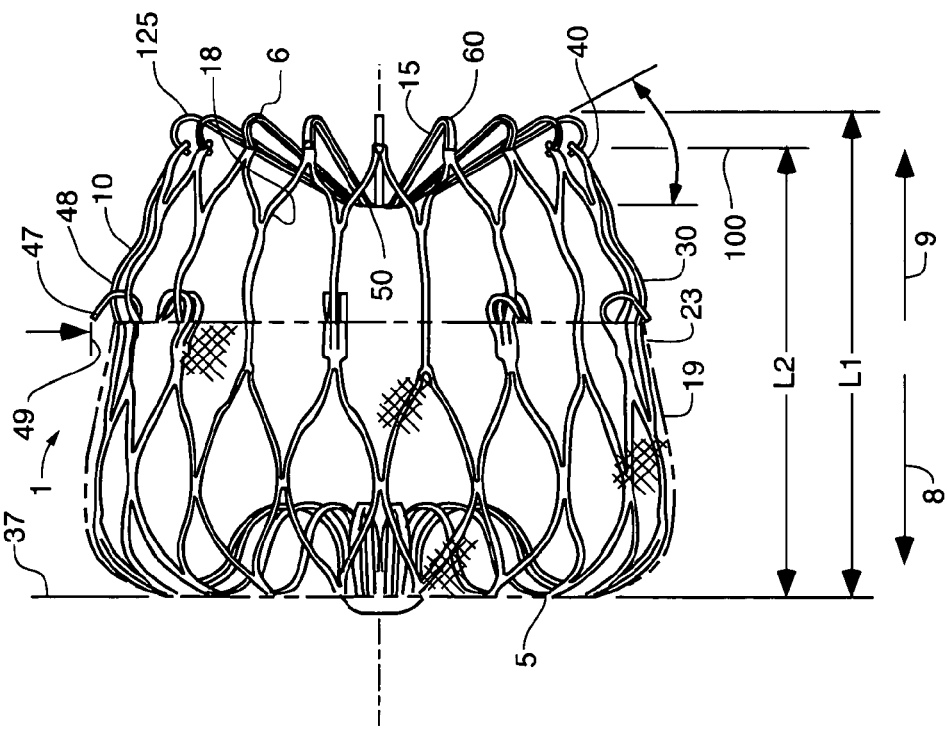
FIG. 1A is a side view of the implanted medical device (IMD)
Figure 1C:
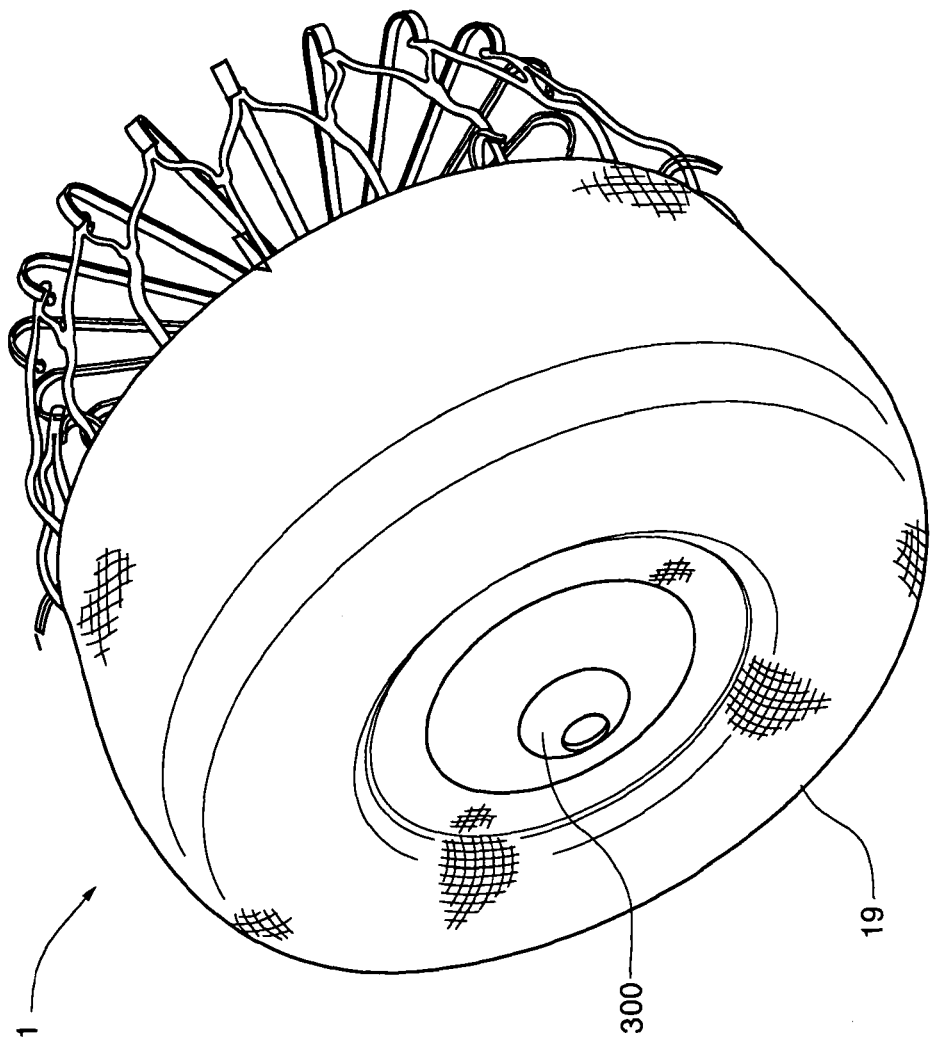
FIG. 1C is a perspective view of the IMD as seen from the proximal end.

FIGS. 1a, 1b and 1c show an exemplary embodiment of an implantable medical device 1 for use occluding the Left Atrial Appendage (LAA) of a patient's heart.

This device is deformable between an expanded, deployed configuration, as depicted in FIGS. 1a, 1b and 1c, and a collapsed configuration presented in FIG. 9.

Figure 16:
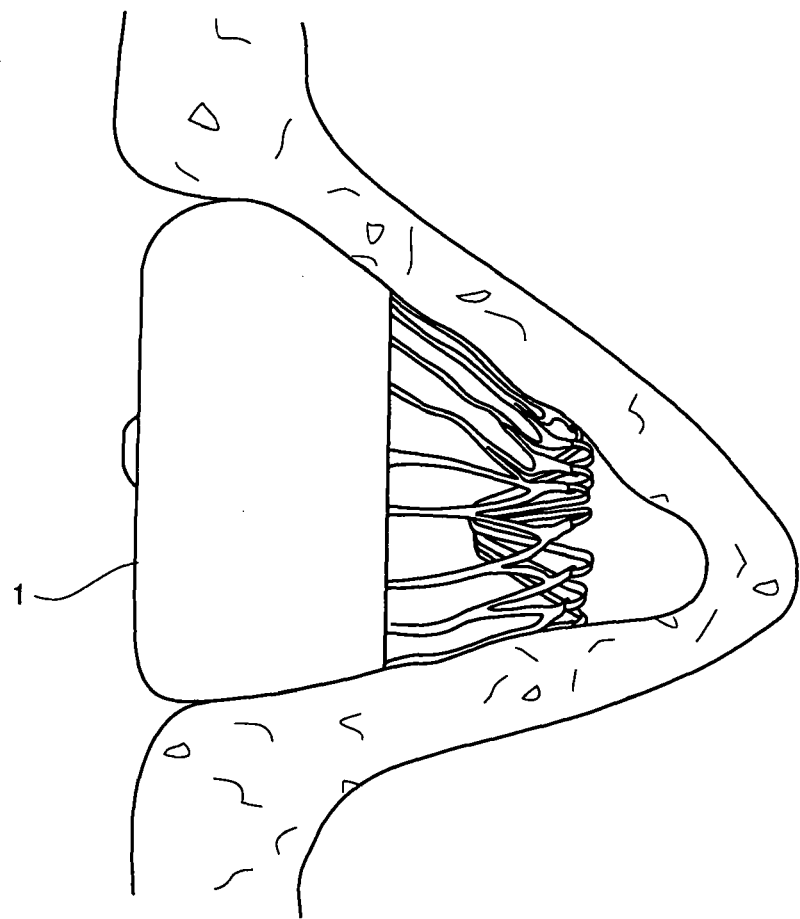
FIG. 16 is a side view of the IMD shown in situ.

In its expanded, deployed configuration, it is suitably sized and shaped to lodge in the LAA, as depicted in FIG. 16.

In its collapsed configuration, the device is suitably sized and shaped to pass through an intravascular delivery device. It is depicted in its collapsed form and is shown in the deployment process in FIGS. 9-13.

The device 1 has a proximal end 5 and an opposite distal end 6 and a longitudinal axis 7. The terms "proximal" and "distal" are used herein for purposes of describing the orientation of device elements and features with respect to one another; the terms are not intended to be limiting. "Proximal" shall correspond to the left portion of the device, as depicted as it is oriented in FIG. 1a, and "distal" shall correspond to the right portion of the device.

Similarly, the terms "posterior" and "anterior" are used herein for purposes of describing the orientation of device elements and features with respect to one another; the terms are not intended to be limiting. "Posterior" shall correspond to the left portion of the device, as depicted in FIG. 1a, and "anterior" shall correspond to the right portion of the device.

The "proximal direction" is depicted by arrow 8 in FIG. 1a and is parallel to the longitudinal axis 7 and points toward the proximal end 5; the "distal direction" is depicted by arrow 9 in FIG. 1a and is parallel to the longitudinal axis 7 and points toward the distal end 6.

Turning to FIG. 1a, the device is seen in its expanded form showing the frame 10 connected to the cap 15 through hinge structures. A membrane 19 is attached to and covers a portion of, the frame 1. A series of barbs typified by barb 47 serve to secure the device in the LAA. The cap 15 intersects with the frame to manage the deployment and recapture of the frame 10 and the barbs 47. Without the cap, the limbs or ribs would tend to unfold at random and interfere with each other. With the cap 15, the deployment of each limb or rib is controlled and regularized so that the limbs cannot get tangled and crossed with respect to one another. The cap 15 does not appreciably extend beyond the length L2 of the frame 10.

Turing to FIG. 1b the device is seen from the distal end in perspective.

Turning to FIG. 1c the device is seen from the proximal end in perspective. In situ, the membrane 19 completely covers the surface exposed to the interior of the heart chamber. A posterior connector 300 is threaded to releaseably couple the device to deployment catheters.

Figure 2:
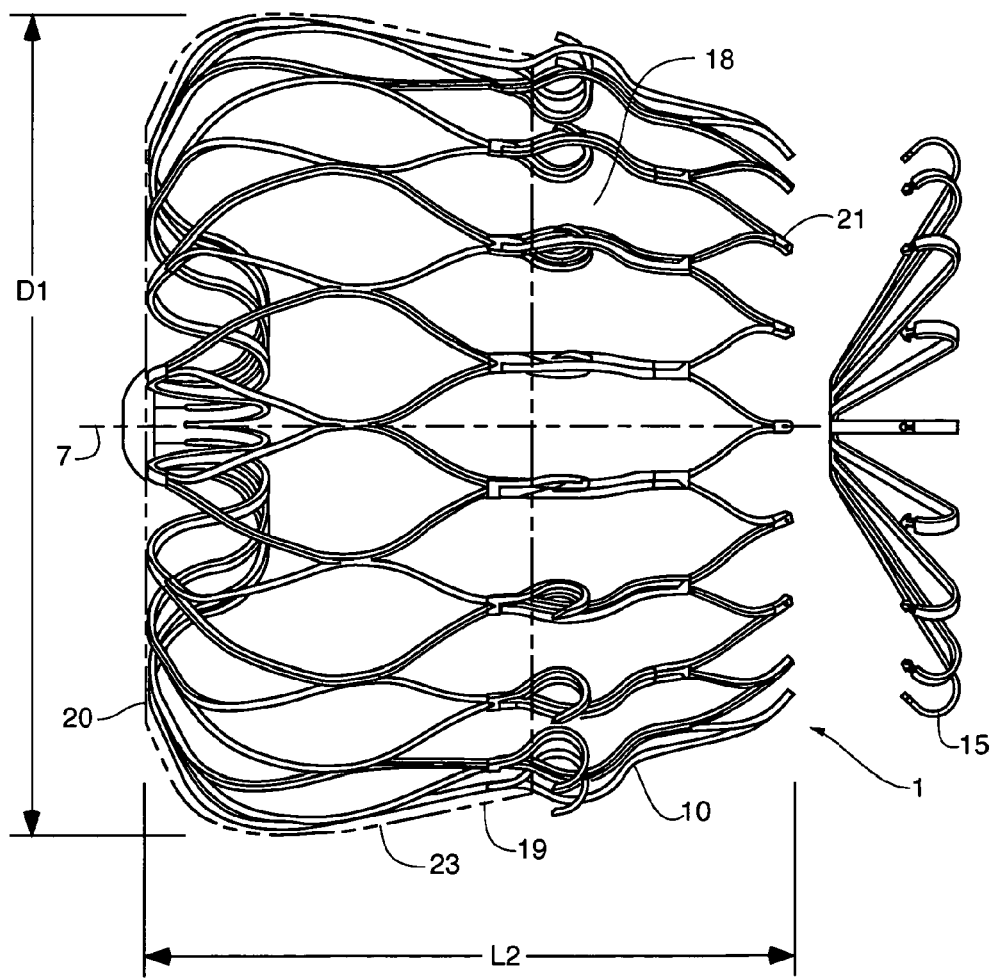
FIG. 2 is a side view of the frame and cap separated.

FIG. 2 depicts the device in an assembly view. The exemplary embodiment of device 1 has a proximal frame 10 and a distal cap 15. The device 1 generally defines an interior space or volume 18. The membrane 19 is connected to and supported by frame 10. This membrane 19 is of a material providing the desired permeability for an intended use. The membrane 19 can be a filter member that blocks the passage of blood clots, but is permeable to blood flow there through. Alternatively, this membrane 19 can be of a material impermeable to blood flow. The membrane 19 may be fabricated from any suitable biocompatible materials. These materials include, but are not limited to, for example, ePFTE (e.g. Gortex.®.), polyester (e.g. Dacron.®.), PTFE (e.g. Teflon.®.), silicone, urethane, metal fibers, and other biocompatible polymers.

The frame 10 has the general shape of a cylinder with one proximal closed end 20 and one distal open end 21 with cylindrical sides 23 there between; in other words, the frame 10 is generally cup-shaped with a terminating open end 21. Yet another way of describing the shape of frame 10 is that it is U-shaped in longitudinal cross-section (i.e. taken through the longitudinal axis 7). The frame 10 has a length L2 in its natural or deployed configuration. The frame 10 is generally circular or annular in horizontal cross-section (i.e. taken perpendicular to the axis 7) and has a diameter D1 in its deployed configuration. In one exemplary embodiment, the aspect ratio between the full length of the device 1 L1 and D1 is approximately 0.5 to 1:5. Due to the flexibility and deformability of frame 10, its dimensions and shape adjust somewhat to suit its deployed environment. More specifically, the proximal end can force the tissues of the LAA into a nearly circular shape to facilitate sealing; i.e. it "drives" tissue. The next portion of the device length gently conforms to the individual structure of the LAA and it effectively follows the LAA shape, i.e. it "follows" the physiology rather than "drives" it.

The membrane 19 covers the closed end 20 of the frame 10 and extends along the sides 23 of the cylindrical wire frame 10. When the device is in position within an LAA, the membrane 19 spans the ostium and intercepts clots or mediates blood flowing in and out of the LAA The membrane 19 can be attached to the frame 10 with stitching or hooks or tangs or stakes.

An exemplary embodiment of the frame 10 or lattice is further illustrated in FIGS. 3a and 3b without the membrane attached. In the embodiment depicted, the device 1 has a unitary construction and is formed from a single elastic metal mesh tube, such as nitinol, that is selectively laser-cut into cells and is then expanded and/or heat shaped and heat treated to create the complex shape depicted in the figure. The frame 10 can be deformed, under the compressive force of a catheter in a manner that will be described in greater detail below with respect to FIGS. 9-13. The frame 10 is suitably shaped so that its cylindrical side walls engage vessel wall tissue to roughly fill the LAA. The frame 10 has a number of roughly S-shaped wire portions, a representative one of which is indicated by reference number 30, that serve as resilient springs to expand the wire frame 10 to its natural or unconstrained size and shape. The S-shaped wire portions emanate from a collar 35 where they are joined to one another or are continuous with one another. The S-shaped curvature of wire portions 30 cause collar 35 to be geometrically recessed relative to a back, or posterior, plane 37 of the wire frame 10.

The opposite distal ends of the frame 10 terminate in limbs, a representative one of which is indicated by reference number 40. Adjacent the terminating ends of limbs 40 are frame joint elements, a representative one of which is indicated by reference number 45. Frame joint elements 45 are hingedly coupled to mating joint elements of cap 15, as will be discussed below with reference to FIGS. 5-8.

The frame 10 includes tissue retention members or barbs 47 located about the periphery of the frame 10. In the exemplary embodiment illustrated, these retention members 47 are barbs that terminate outside of the interior volume 18 defined by the frame 10 and cap 15. The barbs 47, when extended, extend radially outward farther than the adjacent portions of the frame 10. The barbs are oriented to catch tissue to aid in retaining the device 1 in the desired position within an LAA. More specifically, the barbs are oriented to inhibit longitudinal movement of the device 1 in the posterior direction 8.

Figure 15:
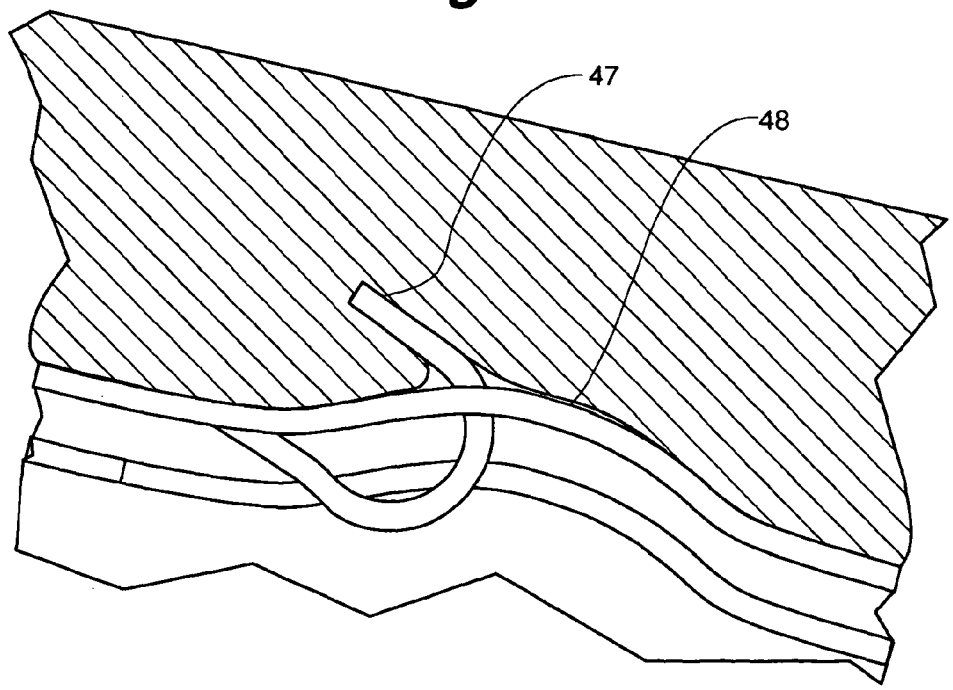
FIG. 15 is an enlarged view of portion of the IMD with one of its barbs engaging surround tissue.

The barbs 47 are adjacent a distended ridge 48 on the frame 10. The distended ridge 48 is a region of the frame 10 that extends radially outward further than the adjacent area of the frame 10. The distended ridge 48 aids in limiting the degree to which the barbs penetrate the tissue to the distance indicated by dimension 49. This is illustrated in FIG. 15.

FIG. 4 shows an exemplary embodiment of a distal cap 15. Distal cap 15 has a central hub 50 from which emanates a number of spokes, a representative one of which is indicated with reference number 55, each having first and second opposite ends 58, 59, where the first ends 58 are connected to the hub 50, and the second ends 59 are terminating ends. The cap 15 is generally symmetrical about longitudinal axis 52. A plane 51 is perpendicular to axis 52 and passes through the posterior-most point of cap 15. In the embodiment illustrated, the cap 15 is a unitary member; that is, the spokes 55 are unitary with or contiguous with the hub

50. The spokes have a natural or spring-biased position, as depicted, in which the spokes are disposed at an angle 53 of between about 0 and 45 degrees with respect to the plane 51. Its complementary angle 54, between the cap's axis 52 and the spokes 50 is, correspondingly between about 90 and 45 degrees.

Between ends 58 and 59, each spoke 55 includes a curved portion 60 that has a radius of curvature 70 that is on the interior of the volume 18 and is circumscribed by the frame and cap when they're assembled as shown in FIG. 1a. The curvature of the curved portion 60 yields an angle 75 of between about 0 and 90 degrees between the terminating end 59 of the spoke and an elongate portion 80 of the spoke that lies between the hub and the curved portion 60.

The terminating end 59 of the spoke 55 provides a cap joint element 90 that couples with a mating frame joint element 45 on frame 10, as will be described below in greater detail with respect to FIGS. 6-9.

The cap 15 is spring-biased to the shape illustrated in FIG. 4. It can be folded, upon application of force, such that the spokes 15 move toward parallel with the axis 52. More specifically, the spokes 55 are hingedly coupled to the hub 50 and are foldable with respect thereto.

The cap 15 is formed of biocompatible materials that provide a spring-biased connection of the spokes to the hub. For example, the cap 15 can be formed of an elastic metal mesh, such as nitinol, cut and heat-shaped to yield the natural, spring-biased configuration shown in FIG. 4.

Additional aspects of the geometry of cap 15 will be appreciated with reference to FIG. 1a. When coupled to the frame 10, the hub 50 of cap 15 is inwardly recessed. In other words, an anterior plane 100 is defined by terminating ends 41 of the limbs 40. This plane is the distal-most part of frame 10. When the cap 15 is coupled to the frame 10, the hub 50 lies posterior to the anterior plane 100. This is the hub's orientation in both the natural, deployed, expanded configuration shown in FIG. 1a, as well as in its compressed configuration for transport within a catheter, as will be described below with reference to FIGS. 9-13. Still another way of expressing this relationship is to note that in both the compressed configuration and the natural configuration, the hub lies between the anterior plane 100 and the posterior plane 37. Yet another way of expressing this relationship is to note that the hub, in the compressed configuration, is substantially enclosed within the frame 10. When the device 1 is compressed, the hub 50 moves relative to the frame 10 in the proximal direction.

As further illustrated in the embodiment of FIG. 1a, when the frame 10 and cap 15 are assembled, each terminating end 41 of the frame 10 is coupled to one spoke 55 of the cap. The longitudinal axis 52 of the cap is colinear with the axis 7 of the frame 10.

The cap 15 performs multiple functions in the device 1. During deployment the cap provides relatively uniform forces on the terminating ends 41 of the limbs 40 so that during deformation between compressed and deployed configurations, and vice versa, the frame 10 is held relatively concentrically about the axis 7. By constraining the ends of the limbs the cap prevents them from becoming entangled and this is an aid to the consistent, predictable and efficient deployment and redeployment of the device. The controlled motion of the limbs during deployment and recapture prevents the barbs from hooking onto companion limbs and breaking or folding or becoming otherwise tangled in the limbs. In use, where several redeployments may be required to achieve proper positioning, this means that fewer devices per procedure are required, thereby reducing the costs associated with the procedure.

Another function of the cap 15 is to provide an atraumatic contact surface at the anterior of the device as it is deployed from a catheter and maneuvered into position. The curved portions 60 of the cap 15 form a bumper portion 125 as will be appreciated from FIG. 1a. This bumper portion 125 extends anteriorly beyond the anterior plane 100 of the frame 10, such that the curved portions 60 would make first contact with tissue. More specifically, the bumper portion 125 extends a distance L1 minus L2 beyond the plane 100.

Turning to FIGS. 5-8, the hinged coupling between the frame 10 and the cap 15 is accomplished through mating joint elements, one male and one female. In the embodiment illustrated and described here, the male element resides on the cap 15 and the female on the frame 10; this configuration however might be swapped. As depicted in FIG. 5, the female joint element 150 is an aperture 155. In the embodiment depicted, the aperture 155 is rectangular and has a width X1 and a length Y1.

Figure 6:
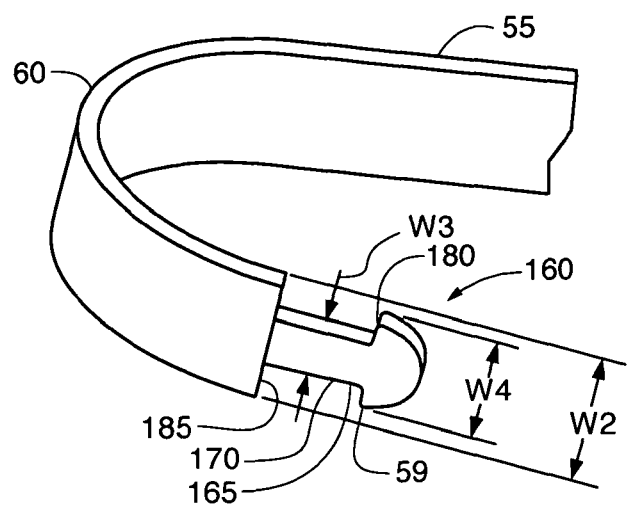
FIG. 6 is a plan view of a hinge portion of the cap.

As depicted in FIG. 6, the male joint element 160 is a tang 165 at the terminating end 59 of the spoke 55. The tang 165 includes a neck 170 having a width W3. The neck 170 extends between a flange 180 and a shoulder 185. The neck 170 is narrower than the flange and shoulder. More specifically, shoulder 185 has a width W2, neck 170 has a width of W3 and flange 180 has a width of W4, where W3 is less than W2 and W4.

Figure 8:
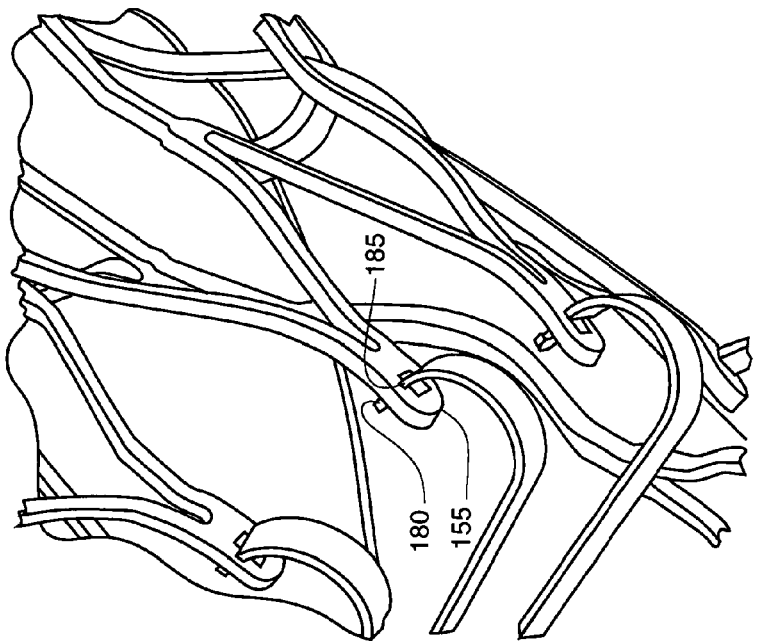
FIG. 8 is a perspective view of the cap to frame hinge connection.
Figure 7:
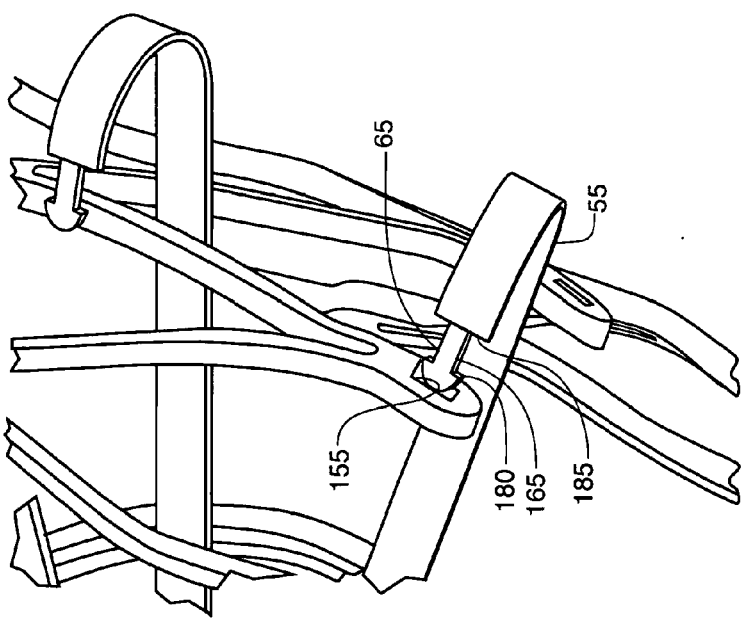
FIG. 7 is a figure showing assembly of the cap and frame.

Male joint element 160, FIG. 6, is sized and shaped to be received by female joint element 150, FIG. 5, and to be held in place. Specifically, Y1 is large enough to accommodate W4; however X1 is smaller than W4. X1 is large enough to accommodate W3. W2 is larger than X1 and Y1. Hence, as depicted in FIG. 7, the cap 15 is coupled to the frame 10 by twisting the spoke 55 somewhat to orient the tang 65 parallel to the length of the aperture 155. The tang 165 is then passed through the aperture 155. When the flange 180 of the tang 165 has cleared the aperture and is let "loose" it springs roughly 90 degrees to its natural orientation, such that the flange 180 and shoulder 185 abut the limb 40 in the area adjacent and defining the aperture 155, thereby holding the spoke 55 against displacement relative to the limb 40, as depicted in FIG. 8.

Although the interlocking structure shown is preferred in this generation of device it is possible to connect the elements with laser welds or the like.

Figure 12:
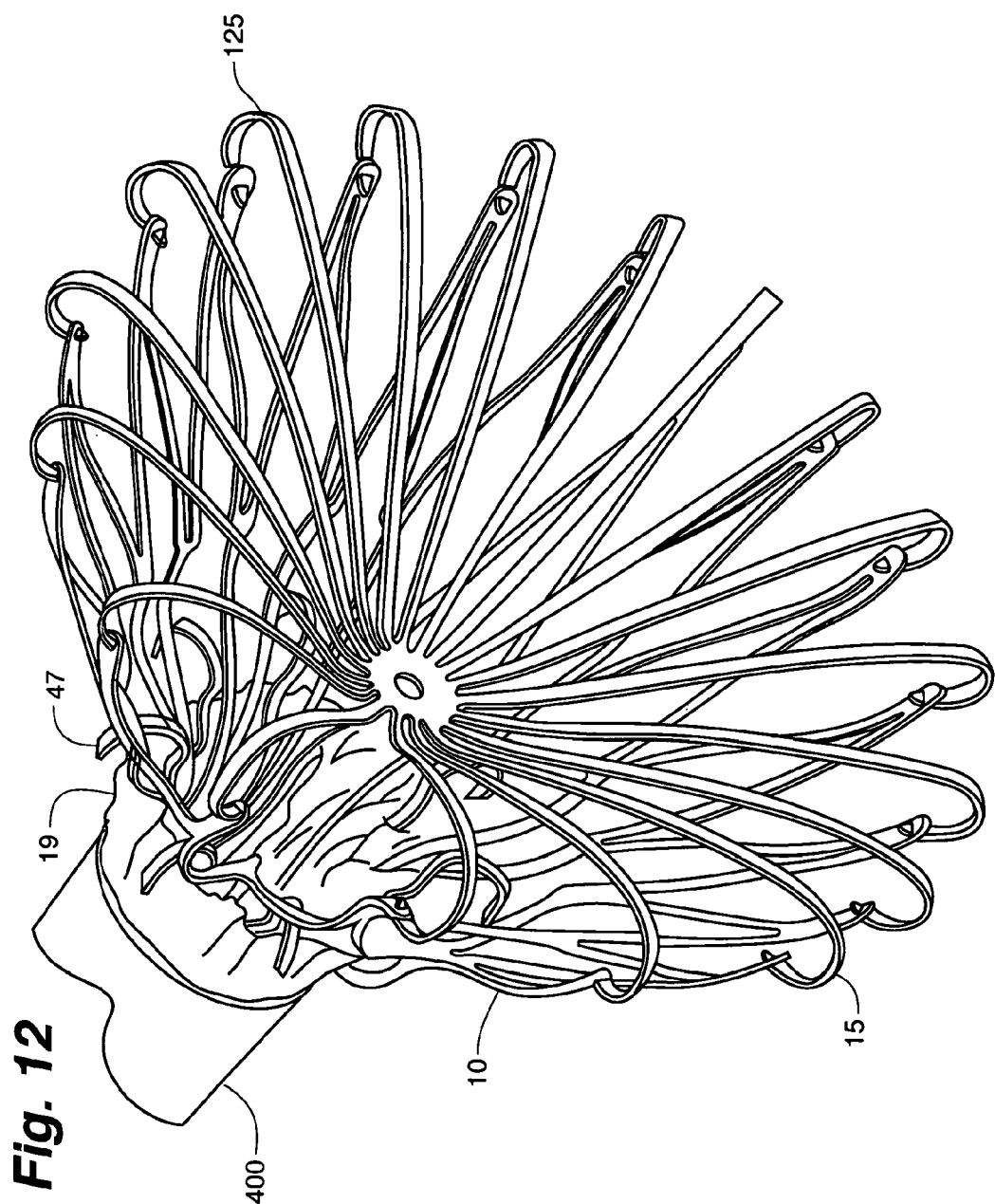
FIG. 12 is a perspective view of the IMD with the cap fully deployed from the delivery catheter.
Figure 13:
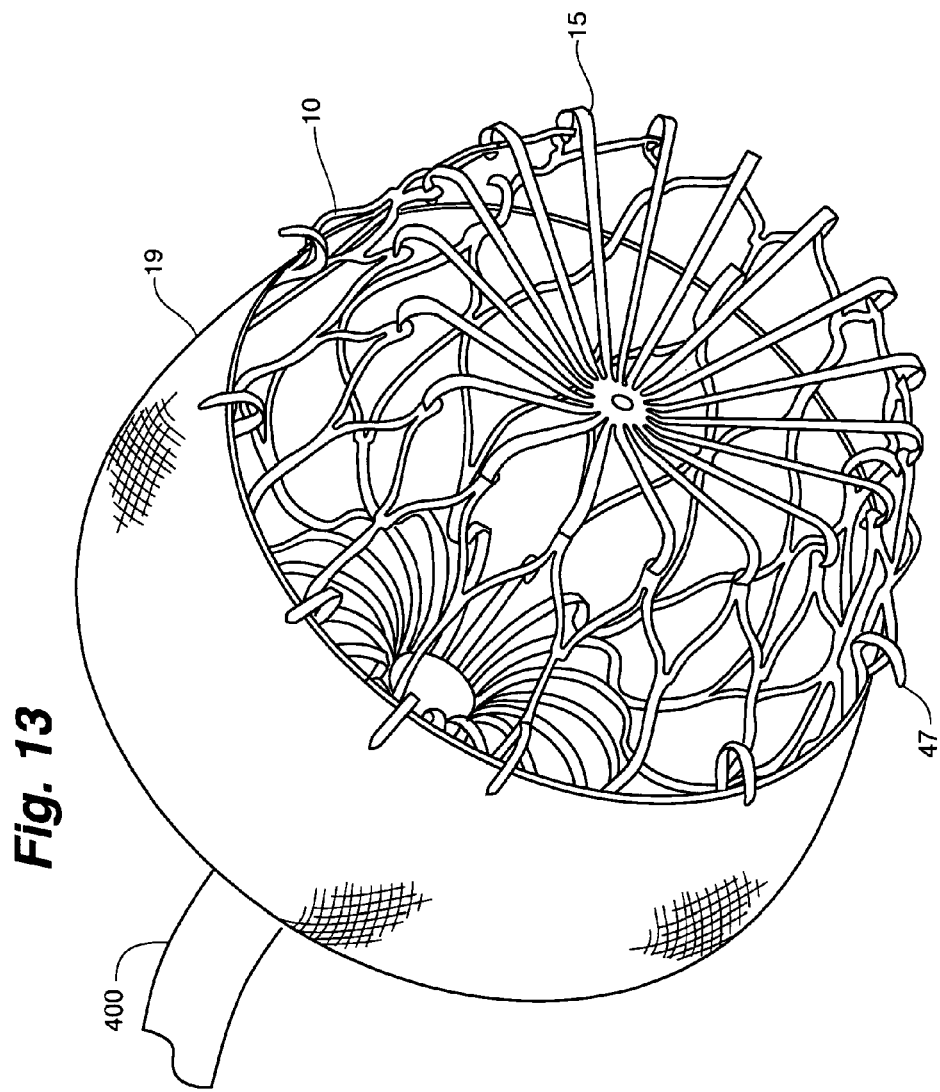
FIG. 13 is a perspective view of the entire IMD deployed from the delivery catheter.
Figure 14A:
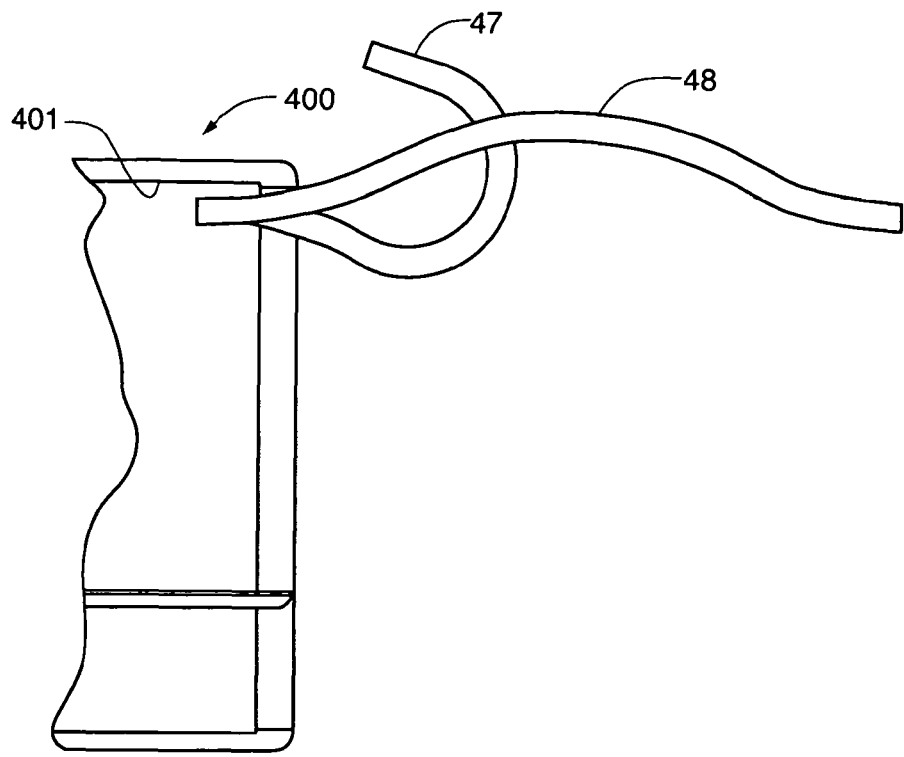
FIG. 14A is a section of the IMD showing the interaction of the barb and the catheter lumen.
Figure 14B:
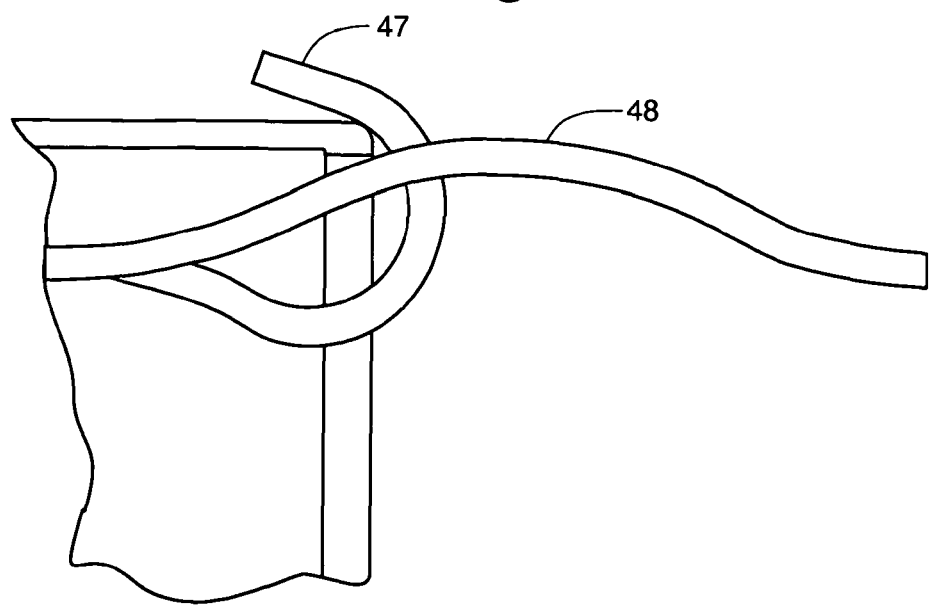
FIG. 14B is a section of the IMD showing the interaction of the barb and the catheter lumen.
Figure 14C:
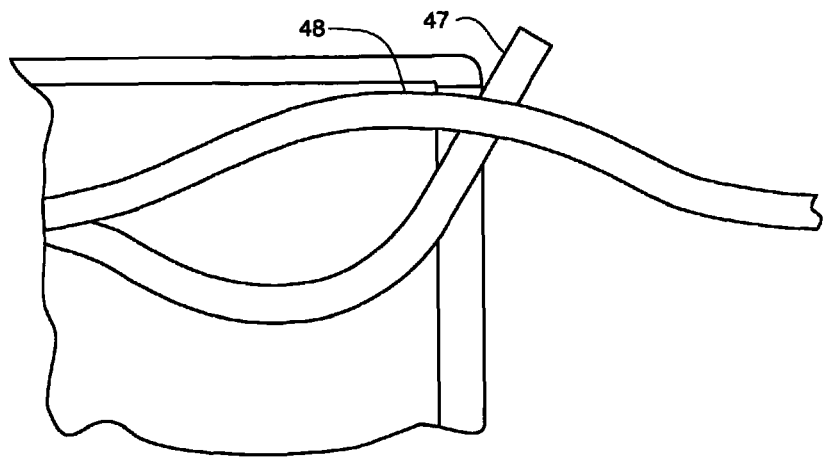
FIG. 14C is a section of the IMD showing the interaction of the barb and the catheter lumen.
Figure 14D:
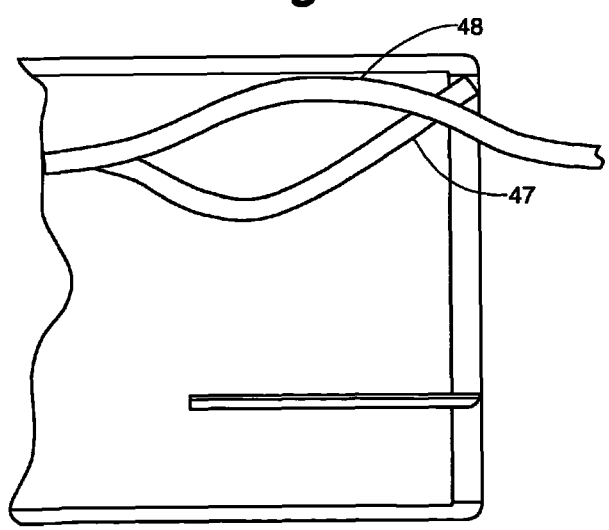
FIG. 14D is a section of the IMD showing the interaction of the barb and the catheter lumen.

To deploy the device 1 in an LAA, the device 1 is tethered to a deployment wire, such as by a screw connection to a posterior connector 300. The device is compressed within a catheter that is then percutaneously coursed through the blood vessel to the desired location. When the end of the catheter is adjacent the desired location, the device is deployed, expanding toward its natural size and shape, as depicted in FIGS. 9-13. FIG. 9 shows the device 1 as it emerges, cap 15 or bumper portion 125 first, from the catheter 400. FIGS. 10-12 show the frame 10 and its cap 15 expanding toward its natural, expanded form, as depicted in FIG. 13. When the device 1 is properly positioned and fully deployed, it is untethered or released from the deployment wire.

As best seen from FIG. 12, the cap 15 radially expands and serves to guide the opening of the radial limbs 40 of the frame 10. The limbs 40 are approximately equally spaced from each other at least in part because of the forces exerted by the cap on the ends 41 of the limbs 40, pulling each limb 40 approximately uniformly radially outward. This action is desirable since it prevents the barbs typified by barb 47 from entangling with other frame cells or structures.

FIGS. 14a-d show the intersection between a constrained barb 47 and the open lumen 401 defined by the delivery catheter 400. During retrieval of the device 1 back into the catheter 400, the ridge 48 and the barb 47 cooperate to fold the barb 47 down so that it can reenter the deployment catheter 49. The wall of the catheter 400 is sufficiently stiff relative to the barb 47 to force the barb 47 to flex into the lumen 401 as seen in the sequence of figures FIGS. 14a-d. The barbs illustrated in FIGS. 14a-d are prevented from rotating into the lumen 401 because the ridge 48 and cell are constrained from rotation by the cap 15 (not shown).

The illustrative embodiment of the device is shown as a two-piece construction. In one embodiment, the linkages between the frame and cap are hinged. In general, the two-piece construction allows for the required mechanical properties to be met with a minimum of complexity and processing. However it should be apparent that the same structure can be achieved with a single piece device. It should also be observed that the two-piece construction allows the device to easily achieve a partitioning of functionality along the length of the device. As noted above, the proximal end can force the tissues of the LAA into a nearly circular shape to facilitate sealing; i.e. it "drives" tissue. The next portion of the device length gently conforms to the individual structure of the LAA and it effectively follows the LAA shape, i.e. it "follows" the physiology rather than "drives" it. The final most distal section of the device with the cap is very compliant and is very blunt so that the device can accommodate the LAA without unnecessary trauma.

As described, the structural features of the device allow for it to be deployed and redeployed without tangling or damage to the device or its retention members. Thus, the device provides for installation of the device according to a method having the following steps:

a) providing an implantable medical device having a frame having retention members extending radially outwardly from said device, a cap connected to said frame and a membrane coupled to and covering a portion of said frame; b) collapsing the device within a delivery catheter; c) implanting the device by deploying the device from said catheter, with the device expanding to its natural state, with retention members engaging adjacent tissue; d) after implanting the device, retracting the device into the catheter; and e) after retracting the device, re-implanting the device by redeploying it from the catheter, with the device expanding to its natural state, with retention members engaging adjacent tissue.

What is claimed is:

1. A device sized and configured for implantation in a left atrial appendage, the device comprising:
a proximal hub;
a frame connected to the proximal hub and extending radially and then distally from the proximal hub, the frame having a proximal portion and an intermediate portion each comprising a plurality of limbs extending between the proximal portion and a distal portion;
wherein the proximal portion extends radially and symmetrically from the proximal hub, the intermediate portion extends distally from a perimeter of the proximal portion as a cylindrical wall when in an unconstrained first configuration of the frame and terminates distally at the distal portion,
wherein the distal portion comprises a plurality of struts which extend radially inward from the plurality of limbs of the intermediate portion; and
wherein the distal portion is at least partially located within the intermediate portion in a collapsed second configuration of the frame and the distal portion advances distally during deployment of the plurality of limbs of the intermediate portion from the collapsed second configuration,
wherein each limb of the plurality of limbs includes a first element in a hinged engagement with a second element of a strut of the distal portion,
a membrane coupled to and covering the proximal portion of each limb of the plurality of limbs of the intermediate portion, wherein the membrane defines a cavity having a distal facing opening, and the membrane comprises a material configured to block a passage of blood clots in a left atrial appendage.

2. The device of claim 1, wherein each limb of the plurality of limbs has a first end and a second end with both of the first end and the second end of each limb positioned proximal a distal end of the distal portion in the unconstrained first configuration.

3. The device of claim 1, further comprising:
a plurality of anchors extending from one or more limbs of the plurality of limbs.

4. The device of claim 3, further comprising:
the membrane comprises a cup-like membrane supported by and covering the proximal portion and at least a portion of the intermediate portion; and
wherein one or more of the plurality of anchors extend from a limb at a position on the limb distal of a distal end of the cup-like membrane.

5. The device of claim 1, further comprising:
a connector extending proximally from the proximal hub, wherein the connector is configured to couple the device to a deployment device.

6. The device of claim 1, wherein each strut of the distal portion forms a rounded distal end of the distal portion.

7. The device of claim 1, wherein the plurality of struts comprise a cap portion.

8. The device of claim 1, wherein one or more struts include at least one bend greater than ninety degrees.

9. A system for implanting an implant in a left atrial appendage, the system comprising:
a delivery catheter having an elongated flexible body with a proximal end and a distal end;
a wire extending through the delivery catheter;
an implant comprising:
a proximal hub;
a plurality of limbs connected to the proximal hub and extending radially and then distally from the proximal hub, the plurality of limbs having a proximal portion and an intermediate portion extending between the proximal portion and a distal portion;
wherein the distal portion is at least partially located within the intermediate portion in a collapsed configuration and the distal portion advances distally during deployment of the plurality of limbs from the collapsed configuration; and
wherein a distal end of the wire is configured to be releasably attached to the proximal hub,
wherein each limb of the plurality of limbs includes a first element in a hinged engagement with a second element of a strut of the distal portion,
a membrane coupled to and covering the proximal portion and at least a portion of the intermediate portion of the plural of limbs, wherein the membrane defines a cavity having a distal facing opening, and the membrane comprises a material configured to block a passage of blood clots in a left atrial appendage.

10. The system of claim 9, wherein each limb of the plurality of limbs has a first end and a second end with both of the first end and the second end of each limb positioned proximal a distal end of the distal portion in a delivery configuration within the delivery catheter and in a deployed configuration.

11. The system of claim 9, further comprising:
a plurality of anchors extending from one or more of the limbs of the plurality of limbs.

12. The system of claim 11, further comprising:
wherein one or more of the plurality of anchors extend from a limb of the plurality of limbs at a position on the limb distal of a distal end of the membrane.

13. The system of claim 9, wherein each limb of the plurality of limbs forms a rounded distal end of the distal portion.

* * * * *